United States Patent [19]

Kobylinski

[11] 4,088,671

[45] May 9, 1978

[54] CONVERSION OF SYNTHESIS GAS USING A COBALT-RUTHENIUM CATALYST

[75] Inventor: Thaddeus P. Kobylinski, Gibsonia, Pa.

[73] Assignee: Gulf Research & Development Company, Pittsburgh, Pa.

[21] Appl. No.: 668,517

[22] Filed: Mar. 19, 1976

[51] Int. Cl.² ............................................. C07C 1/04
[52] U.S. Cl. ...................... 260/449.6 R; 260/449.6 M
[58] Field of Search ......................... 260/449.6, 449 R

[56] References Cited

U.S. PATENT DOCUMENTS

| | | | |
|---|---|---|---|
| 2,354,540 | 7/1944 | Peck | 260/449.6 |
| 2,583,611 | 1/1952 | Sullivan | 260/449.6 |
| 2,636,046 | 4/1953 | Gresham et al. | 260/449.6 |
| 3,988,334 | 10/1976 | Finch | 260/449.6 |

Primary Examiner—Howard T. Mars

[57] ABSTRACT

A process for the synthesis of higher hydrocarbons from the reaction of CO and hydrogen at low pressure is proposed in the contact presence of a catalyst comprising as the active ingredients a major amount of cobalt and a minor amount of ruthenium.

12 Claims, No Drawings

CONVERSION OF SYNTHESIS GAS USING A COBALT-RUTHENIUM CATALYST

This invention relates to a process for the synthesis of higher hydrocarbons from CO and hydrogen in the presence of a novel catalyst containing cobalt and ruthenium at low pressures.

BACKGROUND OF THE INVENTION

The production of higher hydrocarbons by the catalyzed reaction of CO and hydrogen is known familiarly as the Fischer-Tropsch reaction. Commercial plants have operated in Germany, South Africa and other parts of the world based on the use of particular catalysts. The German commercial operation, for example, concentrated on the use of a precipitated cobalt-thoriakieselguhr fixed-bed catalyst, and a later modification where MgO, for economy reasons, replaced part of the thoria.

Nickel is believed to be the original, and thus perhaps the best known, catalyst for the conversion of CO and hydrogen to methane (Sabatier and Senderens — Compt. Rend. 134, 514 (1902); Catalysis Reviews 8, 159 (1973), G. A. Mills and F. W. Steffgen; and Catalysis, Vol. IV, P. H. Emmet, editor — Reinhold Publishing Corp., 1956, p. 109). Cobalt catalysts were later found to be preferred for the synthesis of higher hydrocarbons over the use of nickel since less methane was produced (see "Conversion of Petroleum", Sachanen, 2nd Ed., p. 174). Iron containing catalysts have also been used commercially, for example, in South Africa; but while a spectrum of hydrocarbons are produced, $CO_2$ is also produced as a byproduct, and this is undesirable. (See Paraffins-Chemistry and Technology, by R. Asinger, Pergaman Press, 1968, p. 90 et seq.) Ruthenium is also known as a Fischer-Tropsch catalyst. Ruthenium produces solely methane by the reaction of CO + $H_2$ at atmospheric pressure (see Catalysis Review, 8, 159 (1973), G. A. Mills and F. W. Steffgen). But ruthenium is also known to surpass all other catalysts in the production of high melting waxes at high pressures of 50 to 1000 atmospheres (see Kirk-Othmer Encyclopedia of Chemical Technology, 2nd Ed., Vol. 4, p. 447).

It would thus appear from the prior art that (1) iron catalysts have the disadvantage in Fischer-Tropsch synthesis of producing unwanted $CO_2$; (2) nickel catalysts tend to produce too much methane; (3) cobalt catalysts are preferred for the production of a spectrum of hydrocarbons while avoiding the production of $CO_2$; and (4) ruthenium catalysts produce only methane at low pressure and high melting waxes at very high pressures.

It is also known (see Catalysis, Vol. IV, P. H. Emmet, editor — Reinhold Publishing Corp., 1956, pp. 29–31) that a nickel doped cobalt catalyst increases the methane content of the product over the use of cobalt alone since each component of the catalyst, i.e. nickel and cobalt, tend, as expected, to retain their own peculiar characteristics when the components are combined into a single catalyst. Similarly, U.S. Pat. No. 3,787,468 to Donald Kingsley Fleming et al, entitled "Methanation of Carbon Monoxide and Carbon Dioxide", teaches the addition of ruthenium to a known rhodium or rhodium-platinum-tungsten oxide catalyst for the production of methane from the reaction of CO and hydrogen, or $CO_2$ and hydrogen mixtures, at temperatures in the range of 75° to 250° C. Thus Fleming et al teach the addition of ruthenium to a certain type of mixed metal catalyst does tend to selectively produce methane as shown in FIG. 2 of the patent.

It has now been found in accordance with the invention, and contrary to expectations, that the addition of small amounts of ruthenium to a catalyst containing a major amount of cobalt as the active ingredient in a hydrocarbon synthesis catalyst results in the substantial elimination of methane in the product (rather than an increase in methane) in a low pressure synthesis gas process operated under normal synthesis process reaction temperatures with the simultaneous shift to the production of a higher carbon number product having a lower olefin content.

The surprising feature of the use of a ruthenium promoted cobalt catalyst in the synthesis of hydrocarbons from the reaction of CO and hydrogen is that the benefits of the use of ruthenium which were only achieved previously at very high pressure are now available at substantially atmospheric pressure. Stated another way, it was expected that the synthesis gas process would yield increased amounts of methane in the product when operated at low pressures in the presence of a cobalt catalyst containing small amounts of ruthenium. For reasons not understood, the addition of small amounts of ruthenium to a cobalt synthesis catalyst resulted in the substantial elimination of methane from the product, together with the other benefits noted above, in the production of a more saturated, higher average carbon number product.

DETAILED DESCRIPTION OF CATALYST

The catalyst for use in the present invention comprises as the active catalytic ingredients a major proportion of cobalt and a minor proportion of ruthenium. Essentially and in accordance with the invention, a minor but sufficient amount of ruthenium is added to a cobalt synthesis catalyst to reduce the amount of methane present in the product from the reaction of CO and hydrogen at low pressures and the usual synthesis gas reaction temperatures. The selectivity to methane is less than 25%, usually less than 10%, and most usually less than 2%.

In practice, the cobalt will be distended upon a suitable support to be described below, and the amount of the cobalt in the finished catalyst, i.e. support plus catalytic metals, can be up to 50 weight percent of the finished catalyst, with amounts of cobalt as little as one percent by weight of the finished catalyst being satisfactory. Preferably, the finished catalyst contains a minimum of 5 weight percent cobalt, and more preferably, 10 weight percent cobalt. While the final catalyst can have up to 50 weight percent cobalt as noted above, more usually the catalyst has no more than 40 weight percent cobalt; and more usually, the upper limit of cobalt is about 35 weight percent of the total catalyst. In all instances, the weight percent cobalt is calculated as the metal.

Based on the active catalytic metals which are present (that is, excluding the support material), the ruthenium is present in a minor proportion. Thus the molar ratio of cobalt to ruthenium in the finished catalyst can suitably be from 5:1 to about 200:1, is more usually 10:1 to 100:1, and most usually it is from 15:1 to 80:1. Since the ruthenium is the more expensive component of the catalyst, it is, of course, preferred to employ it in the minimum amount necessary to achieve the desired result. As noted above, the role or function of the ruthenium appears to be to reduce or eliminate the production of methane and $CO_2$ in the reaction product while simultaneously increasing the average molecular weight of the product and decreasing the presence of olefinic products.

The catalytic metals described above are suitably distended on a suitable support material. Generally the supports which can be used for the catalysts of this invention are those inorganic metal oxides which are typically used as catalytic support materials. For example, suitable supports include the oxides of the metals of Groups II, III, IV, V and VIB of the Periodic Chart of the Elements. The oxides of the metals of Groups II, IIIA, and IVB are preferred, e.g. alumina, boria, zinc oxide, magnesia, calcium oxide, strontium oxide, barium oxide, titania, zirconia and vanadia. The most preferred support and the one most widely used from a cost effectiveness viewpoint is, of course, alumina. A combination of metal oxides, such as silica-alumina, are also effective and can be employed. The supports can be synthetically prepared or can be naturally occurring support materials, such as the naturally occurring clays. Specific examples of suitable supports include kieselguhr, carbon, attapulgite clays, diatomaceous earth, activated carbon, coke, charcoal, molecular sieves (both X and Y type), silica, alumina, thoria, zirconia, or mixtures of the above.

The method employed to deposit the catalytic metals of the present invention onto the support material is not critical, and any technique well known to those having ordinary skill in the art to distend the catalytic metals in a uniform thin layer on the catalyst support is suitable here. For example, the cobalt and/or ruthenium can be deposited onto the support material by the technique of minimum excess solution from an aqueous solution of suitable cobalt and/or ruthenium salts, such as the nitrates, chlorides, or acetates; or the cobalt and ruthenium can be co-precipitated from an aqueous solution onto a support by techniques well known in the art. A specific technique is described in the Experimental Work section of this specification.

The catalysts are normally dried, calcined and reduced in a gas such as flowing hydrogen. Normally the cobalt is present as the metal, but some proportion of the cobalt may also be present as the oxide. Similarly, the ruthenium may be present either in the zero valent or oxidized state.

The charge stock for use in the process of this invention is a mixture of carbon monoxide and hydrogen. The source of the CO and hydrogen to be used in the charge stocks for this invention is not critical and can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, and it is preferred to have the $CO_2$ concentration at a level less than 10 volume percent of the charge stock, more preferably less then 1 volume percent. Sulfur compounds in any form are deleterious to the life of the catalyst and should be removed.

The ratio of hydrogen to CO in the charge stock is also not critical and can suitably be from 10:1 to 0.1:1, is preferably from 3:1 to 0.5:1 and is most ususally from 2.5:1 to 1:1.

The product from the synthesis gas reaction is a complicated mixture. However, the stoichiometric relationship between the reactants and products may be illustrated as follows:

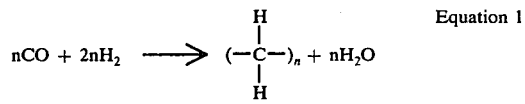

Equation 1

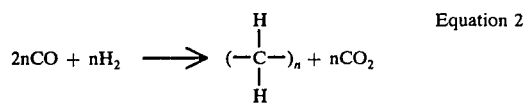

Equation 2

Equations could also be written showing the formation of oxygenated hydrocarbons such as alcohols, aldehydes, ketones and acids. In all of the main reactions, the so-called water-gas shift reaction may occur, as shown in Equation 3:

Equation 3

It is known that the rate of the water-gas shift reaction as shown in Equation 3 above is slow in the presence of a catalyst consisting of cobalt. It has now been found that the addition of ruthenium in small amounts to the cobalt catalyst does not adversely affect this result, and under synthesis conditions the rate of the water-gas shift reaction in the presence of the Co-Ru catalyst is surprisingly even slower than over the Co catalyst, resulting in little $CO_2$ in the product.

In accordance with Equation 1, the product from the synthesis gas reaction is, at least theoretically, a complicated mixture and should contain methane as one of its components. The product recovered using the catalyst of this invention has been found to be substantially methane-free at reaction temperatures of less than 400° C. and to contain only minor amounts of methane, even at temperatures of up to 450° C. In addition, the synthesis gas product of the process of this invention has a higher average carbon number than expected for low pressure operation, and the formation of olefinic products is significantly reduced.

The normal synthesis gas reaction conditions known to those having ordinary skill in the art for the so-called low and medium pressure operations can suitably be used in the process of this invention. Preferably the pressure is about atmospheric to about 50 psig, but reaction pressures as high as 300 psig are contemplated for use with the catalysts of this invention. The reaction temperature is suitably between 60° to 450° C.; is preferably 125° to 400° C., and is most preferably 160° to 350° C. The gaseous hourly space velocity based on the total amount of feed gas is usally from 100 to 1000 volumes of gas per volume of catalyst per hour, with the preferred gaseous hourly space velocity being from 150 to 500 v/v/hour. The synthesis gas reaction using the catalysts of this invention can occur in a fixed, fluid or moving bed type of operation, and the type of operation would not appear to be critical. However, a fixed-bed operation is preferred, and normally the charge gases would be passed upflow through the bed of catalyst and the reaction product would be collected by suitable condensation techniques, after which the products can be separated by fractionation or otherwise.

The invention will be further described with reference to the following experimental work.

Experimental Work

In all of the experiments to be described, a mixture of chemically pure hydrogen and CO (molar ratio 2:1) was passed at a given rate through a preheater and passed upflow at atmospheric pressure through a bed of catalyst maintained at a desired reaction temperature. Effluent from the reactor was analyzed by conventional gas liquid chromatography.

Catalyst Preparation

EXAMPLE 1

(Cobalt Catalyst — No ruthenium)

The catalyst for this Example is the so-called standard cobalt catalyst and was prepared according to literature data (see Catalysis, Vol. 4, P. H. Emmet, editor, Reinhold Publishing Corp., 1956, p. 109). More specifically, the following procedure was employed:

A Solution I was prepared by dissolving:

49.4 grams $Co(NO_3)_2.6H_2O$;
11.0 grams $Mg(NO_3)_2.6H_2O$; and
1.5 grams $Th(NO_3)_2.4H_2O$ in 250 cc of distilled water. Solution II was prepared by dissolving 35 grams $K_2CO_3$ in 250 cc of distilled water. Solutions I and II were separately heated to boiling. Solution I was then added rapidly with vigorous stirring to Solution II, and immediately thereafter, 20 grams of dry powdered kieselguhr were admixed with stirring, and the stirring was continued for 10 minutes. The function of the $K_2CO_3$ Solution II is to co-precipitate the metals as the carbonates onto the kieselguhr.

The mixture was filtered, and the filtrate was washed with distilled water until there was no evidence of nitrates remaining. The filtrate was dried at 120° C. for 16 hours and thereafter calcined at 350° C. for an additional 16 hours. Thereafter the catalyst was reduced at 350° C. in flowing hydrogen for 3 hours.

EXAMPLE 2

(Cobalt + Ru Catalyst)

The catalyst preparation of Example 1 was repeated, except 350 mg of $RuCl_3$ was added to Solution I. The final catalyst was analyzed and found to contain the following:

31.6 wt % cobalt;
3.25 wt % magnesium;
1.98 wt % thoria;
0.53 wt % ruthenium; and
62.64 wt % kieselguhr.

EXAMPLE 3

The catalyst preparation of Example 2 was repeated except that 10 grams of gamma-alumina (surface area 180 m²/g) and 10 grams of MgO were used in place of the 20 grams of kieselguhr. The final catalyst was found to contain:

31.6 wt % cobalt;
2.0 wt % thoria;
0.5 wt % ruthenium;
32.9 wt % alumina; and
32.9 wt % MgO.

EXAMPLE 4

The preparation of the catalyst for Example 3 was repeated except the thorium and magnesium nitrate salts were omitted from Solution I, and the amount of cobalt nitrate was reduced to 21.5 grams in Solution I; and the amount of the potassium carbonate in Solution II was reduced to 17 grams. The final catalyst was found to contain:

17.77 wt % cobalt;
0.70 wt % ruthenium;
40.77 wt % alumina; and
40.77 wt % Mg oxide.

A first series of runs was made using the catalyst from Example 1 (cobalt but no ruthenium), and the results are shown in Table I below:

TABLE I

| Ex. No. | Temperature °C. | CO Conversion % |
|---|---|---|
| 4 | 60 | 0 |
| 5 | 100 | 0 |
| 6 | 150 | 10 |
| 7 | 190 | 60 |
| 8 | 220 | 75 |
| 9 | 300 | 92 |
| 10 | 360 | 98 |

In all of the runs in Table I, the gaseous hourly space velocity based on the total amount of charge gas was 250, and the reaction pressure was, as noted above, atmospheric. The $H_2$ to CO mole ratio was 2:1.

The products obtained from Example 8 (220° C. operation) were analyzed, and the composition of the product gases (less unconverted CO and hydrogen) in weight percent are shown in Table II below.

It should be noted in Table II that the term "Selectivity" in this specification is defined to mean: weight percent of particular product or fraction in the total of all products less $H_2O$, unconverted $H_2$ and CO, and $CO_2$. The gaseous products were found to contain about b 15 volume percent $CO_2$.

TABLE II

| Hydrocarbon Fraction | Selectivity Wt % |
|---|---|
| Methane | 10.1 |
| $C_2$ | 4.8 |
| $C_{3-4}$ | 12.7 |
| $C_{5-8}$ | 31.1 |
| $C_{9-11}$ | 14.3 |
| $C_{12-18}$ | 19.2 |
| $C_{19-32}$ | 6.5 |
| $C_{33}+$ | 1.3 |

Referring to Table II, it can be seen that about 10% of the product is methane. A considerable amount of $CO_2$ (15%) was found in the product, even though the prior art would have indicated otherwise. Further analysis of the $C_9+$ product indicated that about 29% of this product was olefinic in nature.

A second series of runs was made similar to the first series except using the catalyst of Example 2. The results are summarized in Table III below:

TABLE III

| Ex. No. | Temperature °C | CO Conversion % |
|---|---|---|
| 11 | 60 | 28 |
| 12 | 100 | 32 |
| 13 | 150 | 62 |
| 14 | 190 | 70 |

TABLE III-continued

| Ex. No. | Temperature °C | CO Conversion % |
|---|---|---|
| 15 | 220 | 91 |
| 16 | 300 | 97 |
| 17 | 360 | 99 |

A comparison of the results in Tables I and III shows the catalyst of Example 2 (the catalyst of the invention) is more active than the catalyst of Example 1 (cobalt without ruthenium), resulting in higher conversions of CO at lower temperatures. It should be noted that only a trace of $CO_2$ was found in the product.

Again the products obtained from the operation at 220° C. (Ex. 15) were analyzed, and the results are shown in Table IV below:

TABLE IV

| Hydrocarbon Fraction | Selectivity Wt % |
|---|---|
| Methane | 0 |
| $C_2$ | Trace |
| $C_{3-4}$ | 0.6 |
| $C_{5-8}$ | 10.9 |
| $C_{9-11}$ | 11.3 |
| $C_{12-18}$ | 30.9 |
| $C_{19-32}$ | 28.5 |
| $C_{33}+$ | 17.8 |

Referring to Table IV, the product using the catalyst of this invention was methane-free with only a trace of ethane being found. The $C_9+$ product had an olefin content of only 4% compared to the product from Example 8, which was 29% olefinic using the conventional Co catalyst unpromoted with ruthenium.

A comparison of the results from Tables II and IV also shows that 41.9% of the product was $C_9+$ using the conventional Co catalyst, while 88.5% of the product was $C_9+$ using the ruthenium promoted catalyst of this invention.

A series of runs was made at a gaseous hourly space velocity of 380 and varying temperatures using each of the catalysts from Examples 1, 2, 3, and 4 separately to determine the selectivities of the various catalysts for the production of methane as temperature increased. The results are summarized in Table V below:

TABLE V

| Experimental Conditions: | | $H_2:CO = 2:1$, GHSV = 380 | | |
|---|---|---|---|---|
| | | % Selectivity to $CH_4$ Catalyst from Example | | |
| Ex. No. | Temperature °C | 1 (Co) | 2 (Co+Ru) | 3 (Co+Ru) | 4 (Co+Ru) |
| 18 | 200 | 9.8 | 0 | 0 | 0 |
| 19 | 300 | 27.5 | 0 | 0 | 0 |
| 20 | 400 | 48.0 | 0 | 1.2 | 0.5 |
| 21 | 450 | 87.0 | 10.1 | 21.0 | 25.0 |

Referring to Table V, it can be seen that the presence of ruthenium in the cobalt-containing catalysts resulted in the production of a product having substantially less methane. It should be noted that in all the runs in the Table above, only a trace of $CO_2$ was found in the product.

It should also be noted that the substitution of gamma-alumina for kieselguhr in the catalyst for Example 3 has little effect on the production of methane over the product using the catalyst of Example 2. Likewise, the removal of thoria and magnesia (Ex. 4 catalyst compared to Ex. 1 catalyst) had little effect on the production of methane.

The product from Examples 18, 19 and 20 for each of the catalysts was analyzed to determine (1) the percent selectivity to the production of the $C_9+$ fraction and (2) the percent olefins in the $C_9+$ fraction. The results of these analyses are shown in Table VI below:

TABLE VI

| | | % Selectivity to $C_9+$ Fraction Catalyst from Ex. | | | | % Olefins in $C_9+$ Fraction Catalyst from Ex. | | | |
|---|---|---|---|---|---|---|---|---|---|
| No. | Temp. °C | 1 | 2 | 3 | 4 | 1 | 2 | 3 | 4 |
| 22 | 200 | 41 | 88 | 87 | — | 29 | 4 | 5 | 3 |
| 23 | 300 | 30 | 75 | 71 | 73 | 32 | 10 | 9 | 7 |
| 24 | 400 | 18 | 41 | 38 | 34 | 48 | 30 | 26 | 21 |

It can be seen from Table VI that the "% Selectivity to $C_9+$ Fraction" increased using the ruthenium promoted catalysts of this invention (catalyst from Exs. 2, 3, and 4 compared to Ex. 1), and the "% Olefins in $C_9+$ Fraction" was similarly reduced. Again, note that a trace of $CO_2$ was found in the product using the ruthenium promoted catalyst of this invention.

Resort may be had to such variations and modifications as fall within the spirit of the invention and the scope of the appended claims.

I claim:

1. A process for the conversion of synthesis gas consisting essentially of CO and $H_2$ to a product consisting essentially of hydrocarbons and having only minor amounts of methane which comprises contacting said synthesis gas at a temperature of from 60° to 450° C. and a pressure from atmospheric to 300 psig with a catalyst consisting essentially of a major amount of cobalt and a minor amount of ruthenium as the active catalytic components and where in said catalyst the amount of cobalt is from 1 to 50 weight percent, calculated as the metal, and where in said catalyst the molar ratio of cobalt to ruthenium is from 5:1 to about 200:1 and thereafter recovering a product having less than 25 percent methane.

2. A process in accordance with claim 1 wherein the reaction pressure is about atmospheric.

3. A process in accordance with claim 1 wherein the catalyst contains an inert support.

4. A process in accordance with claim 1 wherein the synthesis gas reaction conditions include a temperature from 125° to 400° C.

5. A process in accordance with claim 1 wherein the catalyst is prepared by the co-precipitation of a mixture of ruthenium and cobalt salts onto a support.

6. A process in accordance with claim 5 wherein the support is kieselguhr.

7. A process in accordance with claim 5 wherein the support is gamma-alumina.

8. A process in accordance with claim 5 wherein the molar ratio of hydrogen to CO is about 2:1.

9. A process in accordance with claim 5 wherein the catalyst contains in addition a minor amount of thorium.

10. A process in accordance with claim 1 wherein the amount of cobalt is from 5 to 40 weight percent and wherein the molar ratio of cobalt to ruthenium is said catalyst is from 15:1 to 80:1.

11. A process in accordance with claim 1 wherein the reaction temperature is from 125° to 400° C., the reaction pressure is from atmospheric to 300 psig, wherein the amount of cobalt if from 5 to 35 weight percent, and wherein the molar ratio of cobalt to ruthenium in the finished catalyst is from 10:1 to 100:1, and thereafter recovering a product having less than 10 percent methane.

12. A process for the conversion of synthesis gas consisting essentially of CO and hydrogen to a hydrocarbon product substantially methane-free, which comprises contacting said synthesis gas at a temperature from 160° to 350° C. and a pressure from atmospheric to 50 psig, with a catalyst consisting essentially of a major amount of cobalt and a minor amount of ruthenium distended in a uniform, thin layer on a catalyst support, and where in said catalyst the amount of cobalt is from 10 to 35 weight percent of the total catalyst and wherein the the molar ratio of cobalt to ruthenium in the finished catalyst is from 15:1 to 80:1, and thereafter recovering a hydrocarbon product substantially methane-free.

* * * * *